United States Patent [19]

Vincent et al.

[11] 4,397,857
[45] Aug. 9, 1983

[54] AZABICYCLOOCTANE-CARBOXYLIC ACIDS AND PHARMACEUTICAL COMPOSITIONS CONTAINING THEM AND ANTIHYPERTENSIVE USE THEREOF

[75] Inventors: Michel Vincent, Bagneux; Georges Remond, Versailles; Michel Laubie, Vaucresson, all of France

[73] Assignee: Science Union et Cie, Neuilly-sur-Seine, France

[21] Appl. No.: 313,184

[22] Filed: Oct. 20, 1981

[30] Foreign Application Priority Data

Oct. 21, 1980 [FR] France .............................. 80 22438

[51] Int. Cl.³ ..................... A61K 31/44; C07D 221/22
[52] U.S. Cl. .................................... 424/263; 424/267; 546/84; 546/112
[58] Field of Search ................. 546/112; 424/263, 267

[56] References Cited

U.S. PATENT DOCUMENTS 3,833,562  9/1974  Fonken et al. ............... 260/239 BA

FOREIGN PATENT DOCUMENTS 94175    9/1897   Fed. Rep. of Germany ...... 546/112
1095105  12/1967  United Kingdom ................ 546/112

OTHER PUBLICATIONS

Albrecht, R., et al., *Chem. Ber.* 98, 1431–1434 (1965).

*Primary Examiner*—Richard A. Schwartz
*Attorney, Agent, or Firm*—Gordon W. Hueschen

[57] ABSTRACT

Compounds of the formula

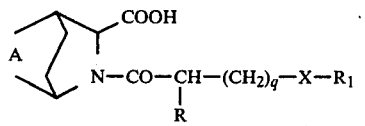

in which A represents a vinylene or dimethylene radical, q is 0 or 1, R is an alkyl radical which can carry an amino group, X represents —S— or —NH—, and $R_1$ is a hydrogen atom or a radical of formula

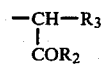

in which $R_2$ is a hydroxy or alkoxy and $R_3$ is a hydrogen atom or an alkyl, cycloalkylalkyl or phenylalkyl radical each having no more than a total of 8 carbon atoms, or an unsubstituted or substituted alkylthioalkyl radical.

These compounds are useful as medicaments, especially anti-hypertensive medicaments.

11 Claims, No Drawings

AZABICYCLOOCTANE-CARBOXYLIC ACIDS AND PHARMACEUTICAL COMPOSITIONS CONTAINING THEM AND ANTIHYPERTENSIVE USE THEREOF

The present invention relates to azabicyclooctanecarboxylic acids, to their preparation and to pharmaceutical compositions containing them.

More especially, it relates to compounds of the general formula (I)

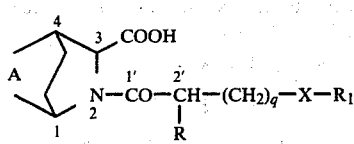

in which
A represents a vinylene or dimethylene radical,
q is 0 or 1,
R represents a lower alkyl radical which can carry an amino group,
X represents —S— or —NH—,
$R_1$ represents a hydrogen atom or a radical of formula

$R_2$ represents a hydroxyl or a lower alkoxy group,
$R_3$ represents a hydrogen atom, a linear or branched alkyl radical, a cycloalkylalkyl radical or a phenylalkyl radical each having no more than a total of 8 carbon atoms, or a radical of formula

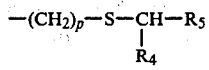

in which
$R_4$ is H, a lower alkyl radical or a ($C_3$ to $C_6$)-cycloalkyl radical,
$R_5$ is H, a ($C_3$ to $C_6$)-cycoalkyl radical or a (lower alkoxy)-carbonyl radical, and
p is 1 or 2.

By lower alkyl or lower alkoxy radicals there are understood groups having from 1 to 4 carbon atoms.

The invention relates also to the salts of compounds of the general formula (I) obtained with a therapeutically compatible mineral or organic base.

The invention relates likewise to the addition salts of the compounds of formula (I) in which X is NH with a therapeutically compatible mineral or organic acid.

The compounds of formula (I) have at least 2 asymmetric carbon atoms. According to the position of the substituents and the degree of hydrogenation, there are from 2 to 8 centres of asymmetry.

The racemic compounds may be split into their diastereoisomeric or epimeric mixtures, or into their enantiomers in known manner. Those various isomers form part of the invention, as do the racemic compounds.

The invention comprises more especially the compounds of the general formula (I) in which X represents NH and $R_3$ represents an alkyl or phenylalkyl group having not more than 8 carbon atoms. In addition, the compounds in which A represents a dimethylene group are preferred and R advantageously represents a methyl group.

The compounds according to the invention and the salts thereof have interesting pharmacological properties. They inhibit especially the transformation of decapeptide angiotensin I into octapeptide angiotensin II by inhibiting the converting enzyme.

The compounds according to the invention have an inhibitory effect on enzymes such as the carboxypolypeptidases or the encephalinases. Their therapeutic use thus makes it possible to reduce, or even to eliminate, the activity of these enzymes by acting on one of the mechanisms directly responsible for hypertension or cardiac insufficiency.

The invention therefore relates to the therapeutic use of the compounds of the general formula (I) and the salts thereof, especially for the treatment of arterial hypertension and cardiac insufficiency.

The invention relates also to the pharmaceutical compositions containing as active ingredient at least one compound of the general formula (I), or one of the addition salts thereof, together with an inert, non-toxic, pharmaceutically acceptable excipient.

For therapeutic use, the compounds of the general formula (I) or the salts thereof are prepared in pharmaceutical forms suitable for intravenous or oral administration. In addition to the active ingredient, the pharmaceutical compositions according to the invention contain one or more inert, non-toxic excipients suitable for pharmaceutical use and/or a binder, an aromatising agent, a disintegrating agent, a sweetener, a lubricant or also a liquid carrier suitable for intravenous administration.

In addition, the pharmaceutical compounds according to the invention may contain another active ingredient having a synergistic or complementary action. Of the latter active ingredients, there may be mentioned a diuretic and, especially, a saliuretic such as, for example, a thiazide, a dihydrothiazide, a chlorosulphamide, a dihydrobenzofuran-2-carboxylic acid or a derivative of phenoxyacetic acid. Examples of such compounds are N-(3'-chloro-4'-sulphamoylbenzamido)-2-methylindoline, ethacrynic acid and furosemide.

It is also possible to add an α-adrenolytic substance, a β-blocker, a calcium antagonist or an agonist of the vascular dopamine receptors.

The useful dosage may very widely depending on the age and weight of the patient, the severity of the therapeutic indication and the method of administration. Oral administration is the preferred method of administration but intravenous administration is also perfectly suitable for the treatment of hypertension.

The unit dose will generally range between 10 and 200 mg.

The invention comprises also a process for preparing the compounds of the general formula (I) according to which an azabicyclooctane-carboxylic acid, or an ester thereof, of the general formula (II)

in which the substituent A has the same meaning as in formula (I) and R' represents a hydroxy or a lower alkoxy, is subjected to the action of a substituted carboxylic acid of the general formula (III)

in which q has the meaning given for formula (I), R″ is a lower alkyl or a protected aminoalkyl, and X′ represents SH or an NH₂ group, each protected by the usual acyl radicals such as, for example, acetyl, benzyloxycarbonyl or tert.-butoxycarbonyl, or one of the functional derivatives thereof, to obtain an acid derivative of the general formula (IV)

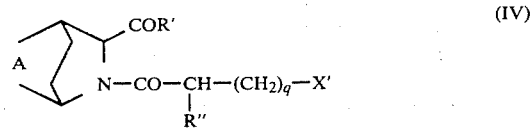

in which the substituents have the meanings mentioned above, which compound is subjected to the usual deprotection processes such as saponification and/or hydrogenolysis and is thus converted into a compound of formula (I) in which $R_1$ is H, and then, if desired, the compound of formula (I) in which $R_1$ is H and X is NH is subjected to a reductive alkylation reaction with a compound of the general formula (V)

$$R_2\text{—}CO\text{—}CO\text{—}R_3 \quad (V),$$

in which $R_2$ and $R_3$ have the meanings given in formula (I), to obtain a compound of formula (I) in which X is NH and $R_1$ is

The intermediate compounds of the general formula (II) are novel and are included in the present invention. They were prepared by a process according to which an imidazo-pyridine of the general formula (VI)

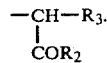

in which A has the meaning given above and $R_6$ is a radical such as optionally substituted phenyl, is subjected to a hydrolysis reaction using one of the usual processes such as boiling with an aqueous solution of sodium hydroxide. The compounds of formula VI are described by BEN-ISHAI and GOLDSTEIN (Tetrahedron 27, pp. 3119–3127 (1971)).

The following Examples illustrate the invention.

EXAMPLE 1

(3RS,2′RS)-N-[3-mercapto-2-methylpropionyl]-2-aza-3-carboxybicyclo[2,2,2]octane

Step A (3RS)-2-aza-3-carboxybicyclo[2,2,2]octane 3.8 g (0.0148 mol) of 8,8a-dihydro-1,3-dioxo-5,8-ethano-2-phenyl-(2H.5H)-imidazo[1,5-a]pyridine (prepared according to D. BEN-ISHAI and E. GOLDSTEIN, Tetrahedron, vol. 27, p. 3119–3127) are suspended in a solution of 30 ml of 4 N sodium hydroxide and 10 ml of methanol. The mixture is heated under reflux for 24 hours, cooled and filtered, and the filtrate is acidified with 30 ml of 4 N hydrochloric acid and then passed over 200 ml of ion exchange resin Dowex 50 H⁺.

After the resin has been washed with distilled water until there are no chloride ions present in the eluate, the desired compound is eluted with 500 ml of 1 N ammonia. When evaporated to dryness, the ammoniacal eluates leave a residue which is the desired product.

Weight: 1.8 g (78%).

Melting point (Kofler block): 253°–255°.

Step B (3RS,2′RS)-N-[3-acetylthio-2-methylpropionyl]-2-aza-3-carboxybicyclo[2,2,2]octane 0.850 g (0.0055 mol) of (3RS)-2-aza-3-carboxybicyclo[2,2,2]octane obtained in the previous step is suspended in a solution of 1.33 g (0.011 mol) of N-dimethylaniline in 40 ml of methylene chloride.

1 g (0.0055 mol) of (2RS)-3-acetylthio-2-methylpropionic acid chloride is added dropwise within 5 minutes to the preceding solution while stirring at room temperature. Stirring is continued for 15 hours. The solution obtained is poured onto a mixture comprising 150 g of crushed ice and 30 ml of a normal aqueous solution of hydrochloric acid. The organic phase is drawn off, washed with N HCl and then with distilled water until it is neutral, dried over CaSO₄, filtered, concentrated to dryness and the evaporation residue is chromatographed over silica (Merck F 254) using a methylene chloride/methanol mixture (95/5) as eluant.

0.550 g (34%) of the desired product is obtained in the form of an oil, the IR and NMR spectra of which conform to the expected structure.

Step C (3RS,2′RS)-N-[3-mercapto-2-methylpropionyl]-2-aza-3-carboxybicyclo[2,2,2]octane Under nitrogen, 0.500 g (0.0017 mol) of (3RS,2′RS)-N-[3-acetylthio-2-methylpropionyl]-2-aza-3-carboxybicyclo[2,2,2]octane prepared in the previous step is dissolved in a mixture of 1.7 ml of normal aqueous sodium hydroxide and 25 ml of ethanol. After 15 hours of contact, the ethanol is evaporated in vacuo and the aqueous solution is extracted with ether, neutralised exactly with 1.7 ml of normal aqueous hydrochloric acid and evaporated to dryness. The residue constitutes the desired product (0.3 g in mixture with 0.0995 g of sodium chloride). The product is tested by NMR in solution in D₂O

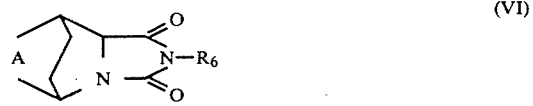

| | |
|---|---|
| 2 H at 1 and 3 | δ = 4.10 and 4.40 ppm |
| 3 H at 2′ and 4′ | δ = 2.3 to 3 ppm |
| 1 H at 4 | δ = 2 to 3 ppm (multiplet) |
| 8 H (4 CH₂) at 5, 6, 7, 8 | δ = 1.7 ppm (block) |

-continued

```
        4
    5  / \  3   COOH
       |   |  /
    6  \ / ─CH
        |  |
        N── 1'   2'    4'
     1 /2 \\
        CO──CH──CH₂──SH
              |
            3'CH₃
```

| 3 H at 3' | δ = 1.5 ppm (doublet) |
|---|---|

Integration is coherent.

EXAMPLE 2

(3RS,4RS,7RS 1'RS)-N-[N-(1-ethoxycarbonylpentyl)-(S)-alanyl]-2-aza-3-carboxybicyclo[2,2,2]oct-5-ene

Step A (3RS,4RS,7RS)-2-aza-3-carboxybicyclo[2,2,2]oct-5-ene 34.5 g (0.119 mol) of 1,3-dioxo-5,8-ethano-2-(4-chlorophenyl)-(2H,5H)-imidazo[1,5-a]pyridine prepared according to BEN-ISHAI et al. (see Ex. 1, A) are heated under reflux under nitrogen for 5 hours with 355 ml (1.42 mol) of aqueous 4 N sodium hydroxide solution.

After cooling to 5°, 14 g of 4-chloroaniline are dried and the filtrate is acidified to pH 1 with concentrated HCl. The filtered solution is passed over 800 ml of resin (Dowex (H+) 50 WX-8). After washing with distilled water until there are no chloride ions present, the desired product is eluted using 2250 ml of 1 N ammonia. The ammoniacal eluates are concentrated to dryness in vacuo by a water jet pump at 40°.

Weight 17.5 g (96.2% of theoretical yield).

| Analysis: $C_8H_{11}NO_2$ | | | |
|---|---|---|---|
| | C % | H % | N % |
| Calculated | 62.72 | 7.24 | 9.14 |
| Found | 62.30 | 6.87 | 9.10 |
| IR: | OH and $NH_2^+$ | | 3600–3200 cm$^{-1}$ |
| | $COO^-$ | | 1630 cm$^{-1}$ |
| NMR: | ($D_2O$ - coherent integration) | | |
| | 4H | 1.3–2.1 ppm | |
| | 2H | 6.5 ppm | 1H  4.3 ppm |
| | 1H | 3.7 ppm | 1H  3.25 ppm |

Step B (3RS,4RS,7RS)-2-aza-3-methoxycarbonylbicyclo[2,2,2]oct-5-ene hydrochloride 1 g (0.00655 mol) of amino acid prepared in the previous step is dissolved in 15 ml of anhydrous methanol and without exceeding +5° 1.5 mol of thionyl chloride are added dropwise. The mixture is heated under reflux for 2 hours then concentrated to dryness in vacuo using a water jet pump at 40°. 1.2 g (90% of theoretical yield) of the desired product are obtained.

m.p.=207 (with decomposition)
IR:
CO (ester) 1740 cm$^{-1}$
$NH_2^+$ 2800–2200 cm$^{-1}$ The crude product is used in the following phase without additional purification.

Step C (3RS,4RS,7RS)-N-[N-(t-butoxycarbonyl)-alanyl]-2-aza-3-methoxycarbonylbicyclo[2,2,2]oct-5-ene 8.9 g (0.044 mol) of ester prepared according to the process described in the previous step are dissolved in 70 ml of dimethylformamide (DMF) in the presence of 6.15 ml (0.044 mol) of triethylamine. To the resulting solution which is maintained at room temperature there are added in succession:

8.3 g of (S)-tert.-Boc.-alanine dissolved in 45 ml of DMF,
6.45 (0.044 mol) of hydroxybenztriazole (HOBT) dissolved in 55 ml of DMF, and
9.05 (0.044 mol) of dicyclohexylcarbodiimide (DCCI) dissolved in 80 ml of chloroform.

After stirring has been carried out for 24 hours, the dicyclohexylurea (DCU) formed is filtered and the filtrate is concentrated to dryness in vacuo by a water jet pump at 50° C. The residue is taken up in 250 ml of ethyl acetate and the solution is filtered and washed in succession with:

2×50 ml of saturated aqueous NaCl solution,
3×50 ml of 10% aqueous citric acid solution,
2×50 ml of saturated aqueous NaCl solution,
3×50 ml of saturated aqueous $NaHCO_3$ solution,
2×50 ml of saturated aqueous NaCl solution, then dried over $CaSO_4$, filtered and concentrated to dryness.

12.8 g (86.5%) of the desired product are obtained in the form of a very viscous oil.

| Analysis: $C_{17}H_{26}N_2O_5$ | | | |
|---|---|---|---|
| | C % | H % | N % |
| Calculated | 60.34 | 7.74 | 8.28 |
| Found | 60.10 | 7.79 | 8.21 |
| IR: | NH | 3400–3300 cm$^{-1}$ | |
| | CO amide | 1700 cm$^{-1}$ and 1510 cm$^{-1}$ | |
| | CO ester | 1750 cm$^{-1}$ | |
| NMR | 2H | (6.1–6.8 ppm) | |
| | 1H | (5.2–5.8 ppm) exchangeable | |
| | 3H | (4.2–4.9 ppm) | |
| | 3H | (3.73 ppm) | |
| | 1H | (3.2 ppm) | |
| | 9H | (1.5 ppm) | |
| | 7H | (1.2–2.2 ppm) | |

Step D (3RS,4RS,7RS)-N-[N-(t-butoxycarbonyl)-(S)-alanyl]-2-aza-3-carboxybicyclo[2,2,2]oct-5-ene 12.8 g (0.038 mol) of the compound obtained in the previous step are dissolved in 140 ml of methanol in the presence of 40 ml of 1 N sodium hydroxide. After stirring has been carried out for 8 hours at room temperature, the solution is concentrated to dryness in vacuo by a water jet pump at 30° and the residue is redissolved in 150 ml of water, extracted with a little ethyl acetate in order to separate the unsaponified material and then acidified with 40 ml of 1 N HCl. The precipitated acid is extracted with 2×100 ml of sulphuric ether and the ethereal solution is dried over $CaSO_4$, filtered and concentrated to dryness. 11.1 g (90% of the theoretical yield) of the desired product are obtained.

| IR: | NH and OH | 3420 cm$^{-1}$ and 3300–2300 cm$^{-1}$ |
|---|---|---|
| | CO (acid and amide) | 1700 cm$^{-1}$ |

-continued

| | | |
|---|---|---|
| | CO (tertiary amide) | 1635 cm$^{-1}$ and 1500 cm$^{-1}$ |
| NMR: | 1H | (8.4 ppm) exchangeable |
| | 2H | (6.3–6.6 ppm) |
| | 1H | (5.5 ppm) exchangeable |
| | 3H | (3.9–4.8 ppm) |
| | 1H | (2.9–3.5 ppm) |
| | 16H | (1–2 ppm) |

Step E (3RS,4RS,7RS)-N-[(S)-alanyl]-2-aza-3-carboxybicyclo[2,2,2]oct-5ene; (compound No. 2 in the following Table):

11.1 g (0.034 mol) of the compound obtained in the previous step are dissolved in 95 ml of methylene chloride and to that solution, cooled to 0, +5°, while stirring, there are added dropwise 75 ml of trifluoroacetic acid in solution in 80 ml of methylene chloride. After 1 hour of contact while stirring at 0, +5°, then 1 additional hour at +25°, the solution is concentrated to dryness in vacuo by a water jet pump then a vane pump (0.1 mm of Hg).

The crude residue (13.6 g) obtained is passed in aqueous solution over resin (DOWEX 50 H+), the resin is washed with distilled water and then the desired product is eluted with 1 liter of 1 N ammonia. Evaporation to dryness of the ammoniacal eluates produces the expected product.

Weight: 6.3 g (83% of theoretical yield)

| | Analysis $C_{11}H_{16}N_2O_3$ | | |
|---|---|---|---|
| | C % | H % | N % |
| Calculated | 58.91 | 7.19 | 12.50 |
| Found | 57.80 | 7.09 | 12.83 |

IR and NMR: see Table.

Step F (3RS,4RS,7RS,1'RS)-N-[N-(1-ethoxycarbonylpentyl)-(S)-alanyl]-2-aza-3-carboxybicyclo[2,2,2]oct-5-ene; (compound No. 8 of the following Table)

1 g (0.045 mol) of the compound obtained in the previous step is dissolved while stirring in 55 ml of anhydrous ethanol in the presence of 13 g of molecular sieve 4 Å and 2.85 g (0.018 mol) of ethyl 2-oxohexanoate (b.p.$_{15}$=89°–91° C., prepared according to P. A. MANIS and M. W. RATHKE, J. Org. Chem. 45 4952–54 (1980)). After stirring has been carried out for 1 hour at room temperature, a solution of 0.28 g (0.0045 mol) of sodium cyanoborohydride in 2.25 ml of anhydrous ethanol is added within 6 hours. Stirring is continued for 15 hours, then the solution is filtered, concentrated to dryness and taken up in 50 ml of aqueous NaCl solution. After extraction with ether to separate the excess keto ester, the aqueous phase is brought to pH 3 with a little 1 N HCl and then extracted with ethyl acetate. The organic phase is dried over CaSO$_4$, then filtered and concentrated to dryness. The evaporation residue is the desired product in the form of the sodium salt.

| | Analysis $C_{19}H_{29}N_2NaO_5$ | | |
|---|---|---|---|
| | C % | H % | N % |
| Calculated | 58.75 | 7.53 | 7.21 |
| Found | 58.74 | 7.71 | 7.48 |

The compounds of the above-mentioned Examples and other compounds of formula (I) prepared in the same manner are listed in the following Table.

| Compound No. | A (chirality of C$_3$) | q | X | R (chirality of C$_{2'}$) | R$_1$ | form |
|---|---|---|---|---|---|---|
| 1 (Ex. 1) | CH$_2$—CH$_2$ (RS) | 1 | S | —CH$_3$ (RS) | H | — |
| 2 (Ex. 2-E) | CH=CH (RS) | 0 | NH | CH$_3$ (S) | H | — |
| 3 | CH$_2$—CH$_2$ (RS) | 0 | NH | CH$_3$ (S) | H | — |
| 4 | CH$_2$—CH$_2$ (RS) | 0 | NH | CH$_3$ (S) | (RS) CH(COOC$_2$H$_5$)CH$_2$—S— | — |
| 5 | CH$_2$—CH$_2$ (RS) | 0 | NH | CH$_3$ (S) | (RS) —CH(COOC$_2$H$_5$)CH$_2$—CH(CH$_3$)$_2$ | sodium salt |
| 6 | CH$_2$—CH$_2$ (R) | 0 | NH | CH$_3$ (S) | (RS) —CH(COOC$_2$H$_5$)CH$_2$CH(CH$_3$)$_2$ | sodium salt |
| 7 | CH$_2$—CH$_2$ (S) | 0 | NH | CH$_3$ (S) | (RS) —CH(COOC$_2$H$_5$)CH$_2$CH(CH$_3$)$_2$ | sodium salt |
| 8 (Ex. 2) | CH=CH (RS) | 0 | NH | CH$_3$ (S) | (RS) —CH(COOC$_2$H$_5$)—nC$_4$H$_9$ | sodium salt |
| 9 | CH$_2$—CH$_2$ (RS) | 0 | NH | —CH$_3$ (S) | (RS) —CH(COOC$_2$H$_5$)—nC$_4$H$_9$ | sodium salt |
| 10 | CH$_2$—CH$_2$ (S) | 0 | NH | —CH$_3$ (S) | (RS) —CH(COOC$_2$H$_5$)—nC$_4$H$_9$ | sodium salt |
| 11 | CH$_2$—CH$_2$ (R) | 0 | NH | —CH$_3$ (S) | (RS) —CH(COOC$_2$H$_5$)—nC$_3$H$_7$ | sodium salt |
| 12 | CH$_2$—CH$_2$ (S) | 0 | NH | —(CH$_3$ (S) | (RS) —CH(COOC$_2$H$_5$)—nC$_3$H$_7$ | sodium salt |
| 13 | CH$_2$—CH$_2$ (S) | 0 | NH | —CH$_3$ (S) | (RS —CH(COOC$_2$H$_5$)—nC$_5$H$_{11}$ | — |

4,397,857

-continued

| Compound No. | A (chirality of $C_3$) | q | X | R (chirality of $C_{2'}$) | $R_1$ | form |
|---|---|---|---|---|---|---|
| 14 | $CH_2-CH_2$ (S) | 0 | NH | $-CH_3$ (S) | (RS)<br>$-CH-COOC_2H_5$<br>\|<br>$CH_2-CH_2-C_6H_5$ | sodium salt |
| 15 | $CH_2-CH_2$ (S) | 0 | NH | $-CH_3$ (S) | (R)<br>$-CH-COOC_2H_5$<br>\|<br>$CH_2-CH_2-C_6H_5$ | trifluoro-acetate |
| 16 | $CH_2-CH_2$ (S) | 0 | NH | $-CH_3$ (S) | (S)<br>$-CH-COOC_2H_5$<br>\|<br>$CH_2-CH_2-C_6H_5$ | trifluoro-acetate |
| 17 | $CH_2-CH_2$ (S) | 0 | NH | $CH_3$ (S) | (RS)             (S)<br>$-CH(COOC_2H_5)-CH_2-S-CH-CH_3$<br>                               $COOC_2H_5$ | sodium salt |

| IR: $\nu_S$ in cm$^{-1}$ | | NMR in CDCl$_3$: chemical shifts ppm/TMS | | | Compound No. |
|---|---|---|---|---|---|
| — | | see Example 1, step C | | | 1 |
| NH,NH$_3^+$, OH: | 3600–2200 | 2H (6.5–6.2) | 2H (4.5–3.5) | 7H (2–1.1) NMR in D$_2$O. | 2 |
| C=O: | 1650–1550 | 1H (5.1) | 1H (3) | | |
| NH, OH: | 3600–2400 | 3H (4.5–3.7) | 8H (1.65) | NMR in D$_2$O | 3 |
| C=O: | 1650–1550 | 1H (2.15) | 3H (1.4–1.1) | | |
| NH$_2^+$: | 3500–2500 | 2H (5.8) exchangeable | 26H (2.3–0.1) | | 4 |
| C=O ester: | 1725 | 8H (4.5–2.8) | | | |
| C=O amide: | 1625 | | | | |
| NH: | 3300 | 7H (4.5–3) | | | 5 |
| C=O ester: | 1720 | 24H (2.5–0.7) | | | |
| C=O amide: | 1650–1580 | | | | |
| NH,OH: | 3320 | 1H (4.8) exchangeable | 24H (1) | | 6 |
| C=O ester: | 1725 | 6H (2.5–0.5) | | | |
| C=O amide: | 1610 | | | | |
| NH, OH: | 3320 | 1H (4.5–3) exchangeable | 24H (0.95) | | 7 |
| C=O ester: | 1725 | 6H (2.5–0.7) | | | |
| C=O amide: | 1610 | | | | |
| NH$_2^+$, OH: | 3600–2300 | 1H (8) exchangeable | 6H (4.7–3.1) | | 8 |
| C=O ester: | 1735 | 2H (6.5) | 20H (2.4–0.8) | | |
| C=O amide: | 1640 | | | | |
| NH$_2^+$: | 2700–2300 | 2H (7.5) exchangeable | 24H (2.5–0.6) | | 9 |
| OH: | 3600–3200 | | | | |
| C=O ester: | 1730 | 6H (4.7–3.5) | | | |
| C=O amide: | 1630 and 1540 | | | | |
| NH, OH: | 3400 | 7H (4.6–2.9) | | | 10 |
| C=O amide: | 1610 | 24H (2.5–0.7) | | | |
| C=O ester: | 1725 | | | | |
| NH, OH: | 3600–3100 | 7H (4.5–3) | | | 11 |
| C=O ester: | 1725 | 22H (2.6–0.8) | | | |
| C=O amide: | 1620 | | | | |
| NH, OH: | 3600–3100 | 7H (4.7–3) | | | 12 |
| C=O ester: | 1725 | 22H (2.6–0.3) | | | |
| C=O amide: | 1620 | | | | |
| NH, OH: | 3600–2300 | 2H (6.2) exchangeable | 26H (2.5–0.6) | | 13 |
| C=O ester: | 1725 | 6H (4.5–2.5) | | | |
| C=O amide: | 1630 | | | | |
| NH, OH: | 3300 | 5H (7.3) | 19H (3–1) | | 14 |
| C=O ester: | 1725 | 6H (4.5–3) | | | |
| C=O amide: | 1615 | | | | |
| NH, OH: | 2800–2300 | | | | 15 |
| C=O ester: | 1730 | | | | |
| C=O amide: | 1670 and 1630 | | | | |
| NH$_2^+$, OH: | 3200–2200 | 3H (8.35) exchangeable | 6H (4.8–3.7) | 12H (2.2–1.6) | 16 |
| C=O ester: | 1730 | 5H (7.35) | 4H (3–2.2) | 3H (1.4) | |

| IR: $\nu_S$ in cm$^{-1}$ | | NMR in CDCl$_3$: chemical shifts ppm/TMS | Compound No. |
|---|---|---|---|
| C=O amide: | 1620 | | 18 |
| NH, OH: | 3400 | 11H (4.6–2.8) | |
| C=O ester: | 1725 | 22H (2–1) | |
| C=O amide: | 1615 | | |

Pharmacological study of the compounds of the invention

The compounds according to the invention were tested by i.v. or p.o. administration to dogs during consciousness.

The arterial blood pressure of the dogs was measured by means of a pressure detector (Statham P 23 Db) after catheterisation of the aorta through the femoral artery. The findings were recorded by means of a recording apparatus (Brush 400).

Angiotensin I and angiotensin II are injected into the animals intravenously at a dosage of 0.3 γ/kg. A dose-/activity curve is established for each of those hormones. The compounds according to the invention are then administered orally or intravenously at a dosage of from 1 to 100 mg/kg. A second dose/activity curve is then established for angiotensin I and angiotensin II after administration of the product tested.

It was observed that there was an inhibition of the hypertensive effect ranging from 50 to 100% which occurred from 30 to 90 minutes after administration and which remained at from 40 to 80% more than 6 hours after administration. Certain compounds remained active after 24 hours, which is not the case with any compound of this type known hitherto. In addition, the compounds of the invention have no acute toxicity (LD$_O$ > 500 m/kg i.p. in mice).

Example of Formulation

| | |
|---|---|
| (3RS,2'RS)-N—[3-mercapto-2-methylpropionyl]-2-aza-3-carboxybicyclo[2,2,2]octane | 20 g |
| wheat starch | 105 g |
| corn starch | 90 g |
| casein treated with formaldehyde | 20 g |
| magnesium stearate | 15 g |
| talc | 20 g |
| for 1000 tablets. | |

What is claimed is:

1. A compound having the formula

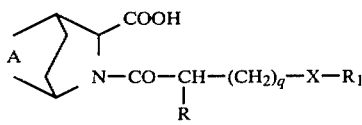

(I)

in which
A represents a vinylene or dimethylene radical,
q is 0 or 1,
R represents a lower alkyl radical which can carry an amino group,
X represents —S— or —NH—,
R$_1$ represents a hydrogen atom or a radical of formula

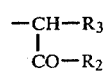

R$_2$ represents a hydroxyl or a lower alkoxy group,
R$_3$ represents a hydrogen atom, a straight or branched alkyl radical, a cycloalkylalkyl radical or a phenylalkyl radical each having no more than a total of 8 carbon atoms, or a radical of formula $$-(CH_2)_p-S-\underset{R_4}{CH}-R_5$$

in which
R$_4$ is H, a lower alkyl radical or a (C$_3$ to C$_6$)-cycloalkyl radical,
R$_5$ is H, a (C$_3$ to C$_6$)-cycloalkyl radical or a (lower alkoxy)carbonyl radical, and
p is 1 or 2,
in their racemic form or as optical isomers or the salt thereof obtained with a therapeutically compatible organic or mineral base or the addition salt of the compound of formula (I) in which X is NH with a therapeutically compatible mineral or organic acid.

2. A compound according to claim 1 having the formula (I) in which
A represents a dimethylene group.

3. A compound according to claim 1 or claim 2 having the formula (I) in which X represents NH and R$_3$ represents an alkyl or a phenylalkyl group having not more than 8 carbon atoms.

4. A compound according to any of claims 1 to 3 having the formula (I) in which R is a methyl group.

5. Compound of claim 1 being (3RS,2'RS)-N-[3-mercapto-2-methylpropionyl]-2-aza-3-carboxybicyclo[2,2,2]octane or the (S) isomer thereof.

6. Compound of claim 1 being (3S,1'RS)-N-[N-(1-ethoxycarbonyl-3-methylbutyl)-(S)-alanyl]-2-aza-3-carboxybicyclo[2,2,2]octane, or the (S) isomer thereof or the sodium salt of these.

7. Compound of claim 1 being (3S,1'RS)-N-[N-(1-ethoxycarbonyl-3-phenylpropyl)-(S)-alanyl]-2-aza-3-carboxybicyclo[2,2,2]octane, or the (S) isomer thereof or the sodium salt or the trifluoroacetate of these.

8. Pharmacetucial composition useful as an antihypertensive containing as active ingredient an effective antihypertensive amount of at least one compound according to any one of the claims 1 to 7 as well as an excipient or a suitable non-toxic inert carrier.

9. A method for treating a patient suffering from hypertension, which comprises administering to said patient a therapeutically effective dose of a compound according to claim 1.

10. A method according to claim 9 wherein the therapeutically effective dose is between 10 and 200 mg.

11. A compound having the formula (II)

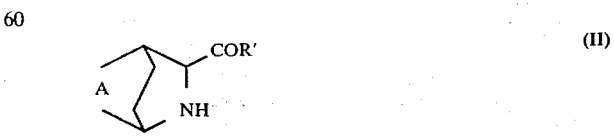

(II)

in which A has the same meaning as in formula (I) according to claim 1 and R' represents a hydroxy or lower alkoxy group.

* * * * *

UNITED STATES PATENT AND TRADEMARK OFFICE
CERTIFICATE OF CORRECTION

PATENT NO. : 4,397,857
DATED : August 9, 1983
INVENTOR(S) : Michel Vincent, Georges Remond and Michel Laubie It is certified that error appears in the above—identified patent and that said Letters Patent is hereby corrected as shown below:

Title Page, [73] Assignee: "Science Union et Cie" should read -- ADIR --

Col. 1, lines 7 & 8; "azabicyclooctanecarboxylic" should read
-- azabicyclooctane-carboxylic --
Col. 7, line 13; "-5ene;" should read -- -5-ene; --
Cols. 7 & 8, the large table at the bottom of the page, "Compound 4", the 7th
column; "$CH(COOC_2H_5)CH_2-$" should read -- -- $CH(COOC_2H_5)CH_2-$ --
Cols. 7 & 8, the large table at the bottom, 7th column, second to the last
line; "(RS" should read -- (RS) --
Col. 11, line 24; "100" should read -- 10 --
Col. 11, line 25; "ten" should read -- then --
Col. 11, line 25; "angiostensin" should read -- angiotensin --
Col. 12, line 7; the line starting with "$R_2$" and ending in "group," should
be printed below the table line.
Col. 12, line 48; "Pharmacetucial" should read -- Pharmaceutical --

Signed and Sealed this

Twenty-ninth Day of November 1983

[SEAL]

Attest:

GERALD J. MOSSINGHOFF

Attesting Officer    Commissioner of Patents and Trademarks